US006642198B2

(12) United States Patent
Pflederer et al.

(10) Patent No.: US 6,642,198 B2
(45) Date of Patent: *Nov. 4, 2003

(54) CLEAR CLEANSING DETERGENT SYSTEMS

(75) Inventors: Christine A. Pflederer, Monmouth Jct., NJ (US); Joseph J. Librizzi, Neshanic, NJ (US); Delores M. Santora, Somerville, NJ (US); Diana L. Friscia, Fairless Hills, PA (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 22 days.

(21) Appl. No.: 09/454,874

(22) Filed: Dec. 3, 1999

(65) Prior Publication Data

US 2002/0123438 A1 Sep. 5, 2002

Related U.S. Application Data

(60) Provisional application No. 60/112,492, filed on Dec. 16, 1998.

(51) Int. Cl.[7] .............................. C11D 3/22; C11D 3/37; C11D 15/00; A61K 7/00
(52) U.S. Cl. ...................... 510/434; 510/119; 510/130; 510/413; 510/421; 510/470; 510/476; 510/477; 510/488; 510/533; 424/487; 424/70.16
(58) Field of Search ................................ 510/119, 130, 510/413, 434, 476, 477, 488, 533, 421, 470; 424/487, 70.16

(56) References Cited

U.S. PATENT DOCUMENTS

| | | | |
|---|---|---|---|
| 2,768,080 A | 10/1956 | Hellman et al. ................ 95/7 |
| 3,708,445 A | 1/1973 | Junas ............................ 260/4 |
| 3,759,861 A | 9/1973 | Shimokawa ................ 260/31.4 |
| 4,009,259 A | 2/1977 | Ament et al. .................. 424/89 |
| 4,080,310 A | 3/1978 | Ng et al. .................... 252/544 |
| 4,138,381 A | 2/1979 | Chang et al. .............. 260/29.6 |
| 4,375,421 A | 3/1983 | Rubin et al. ................ 252/110 |
| 4,384,095 A | 5/1983 | Reed et al. .................. 526/293 |
| 4,443,362 A | 4/1984 | Guth et al. .................. 252/545 |
| 4,552,685 A | * 11/1985 | Kernstock et al. ........... 252/355 |
| 4,657,690 A | 4/1987 | Grollier et al. ............... 252/90 |
| 4,664,835 A | 5/1987 | Grollier et al. ............... 252/90 |
| 5,009,813 A | 4/1991 | Watanabe et al. ........... 252/545 |
| 5,106,613 A | 4/1992 | Hartnett et al. ............... 424/71 |
| 5,124,078 A | 6/1992 | Baust ......................... 252/546 |
| 5,358,667 A | 10/1994 | Bergmann ................... 252/547 |
| 5,391,368 A | 2/1995 | Gerstein .................. 424/70.13 |
| 5,597,406 A | 1/1997 | Fischer et al. .............. 106/237 |
| 5,597,407 A | 1/1997 | Fischer et al. .............. 106/237 |
| 5,607,980 A | 3/1997 | McAtee et al. ............. 514/476 |
| 5,641,479 A | * 6/1997 | Linares et al. ............ 424/70.21 |
| 5,661,189 A | 8/1997 | Grieveson et al. .......... 514/784 |
| 5,711,899 A | 1/1998 | Kawa et al. ................. 252/311 |
| 5,716,919 A | 2/1998 | Sano .......................... 510/159 |
| 5,747,435 A | 5/1998 | Patel ......................... 510/119 |
| 5,968,496 A | * 10/1999 | Linares et al. ........... 424/70.21 |
| 6,090,773 A | * 7/2000 | Lukenbach et al. ......... 510/475 |

FOREIGN PATENT DOCUMENTS

| | | |
|---|---|---|
| CA | 1888043 | 5/1985 |
| CA | 2033626 | 7/1991 |
| CA | 2039963 | 10/1991 |
| CA | 2040547 | 10/1991 |
| CA | 2070299 | 12/1992 |
| CA | 2086689 | 7/1993 |
| CA | 2095743 | 11/1993 |
| CA | 2210971 | 5/1996 |
| CA | 2211004 | 5/1996 |
| CA | 2101843 | 10/1997 |
| CA | 2211321 | 1/1998 |
| CA | 2211754 | 2/1998 |
| CA | 2211777 | 2/1998 |
| EP | WO 92/13513 | * 8/1992 |
| FR | 2650291 | 2/1991 |
| WO | WO/92/13513 | 8/1992 |
| WO | WO93/24101 | 12/1993 |
| WO | WO97/26860 | 7/1997 |
| WO | WO 97/26860 | * 7/1997 ............ A61K/7/50 |

OTHER PUBLICATIONS

Aculyn, Rohm & Haas 1990 Article: Aculyn™ 22 Thickner Mar. 1990.
Formulary–published in happi/Jul., 1999 issue, p. 16–re: Clear, Mild Shower Gel, #xp002136053.

* cited by examiner

*Primary Examiner*—Brian P. Mruk
(74) *Attorney, Agent, or Firm*—Michele G. Mangini

(57) ABSTRACT

The present invention is directed to detergent compositions that not only have superior viscosity, spreadability, and clarity properties but also do not cause significant irritation to the skin and eyes. More specifically, acrylic polymeric thickeners are combined with polyol glycol thickeners in order to achieve such properties in detergent compositions.

29 Claims, No Drawings

CLEAR CLEANSING DETERGENT SYSTEMS

CROSS-REFERENCE TO RELATED APPLICATION

This Application claims the benefit of U.S. Provisional Application No. 60/112,492 filed on Dec. 16, 1998, which is incorporated by reference in its entirety.

FIELD OF THE INVENTION

The present invention is directed to a clear, thickened detergent composition having superior clarity and spreadability, and methods for thickening such compositions. More specifically the present invention is directed to such compositions thickened with both a hydrophobically modified acrylic polymeric thickener and a polyol alkoxy ester thickener.

BACKGROUND OF INVENTION

Surfactant systems that are mild to hair, skin, eyes, and ocular mucosa, such as that found in "NO MORE TEARS" ® baby shampoo available from Johnson & Johnson Consumer Companies, Inc., were developed in order to lessen eye sting during the shampooing process. Another way to further lessen the chance of eye sting is by thickening the resulting surfactant composition with the goal of minimizing the opportunity for the product to flow into the eyes.

A well-known thickener in the art are the polyol alkoxy esters. However, when such thickeners are added to detergent compositions at high concentrations, the resulting detergent compositions become relatively hazy and possess poor spreading characteristics.

Other well-known thickeners include the hydrophobically modified acrylic polymers. Although the use of these thickeners at relatively high concentrations will not deleteriously affect the clarity of the detergent compositions, the resulting compositions are not only irritating to the eyes but also fail to produce a detergent composition having a viscosity within the range suitable for gels.

Accordingly, it would be highly desirable to find a thickener or combination of thickening agents that will provide highly viscous, clear detergent compositions that are relatively mild to the skin and eyes.

SUMMARY OF INVENTION

The present invention relates, in one of its aspects, to a detergent composition comprising:

a) a hydrophobically modified acrylic copolymer thickener;

b) a polyol alkoxy ester thickener; and c) at least one surfactant selected from the group consisting of an anionic surfactant, a non-ionic surfactant, an amphoteric surfactant, a betaine surfactant, and mixtures thereof, wherein the composition contains greater than about 1%, based upon the total weight of the composition, of the polyol alkoxy ester thickener.

Another embodiment of the present invention is directed to a method for improving the clarity of a polyol alkoxy ester-containing detergent composition comprised of a) combining a sufficient amount of a hydrophobically modified acrylic thickener with said composition under conditions sufficient.

Yet another embodiment of the present invention is directed to a method for improving the spreadability of a detergent composition comprised of a) adding a sufficient amount of a hydrophobically modified acrylic thickener and a sufficient amount of a polyol alkoxy ester to the detergent composition under conditions sufficient.

We have unexpectedly found that surfactant-containing compositions containing both a hydrophobically modified acrylic thickener and a polyol alkoxy ester are not only clear, sufficiently viscous, and possess superior spreadability properties, but they are also relatively mild to the skin and eyes.

DETAILED DESCRIPTION OF INVENTION

For purposes of this invention, the term "pH responsive" shall mean that the properties and characteristics of the acrylic copolymer vary with pH. More specifically, the acrylic copolymer is generally insoluble at a pH of less than about 2, but dissolves or swells in an aqueous solution that possesses a neutral or alkaline pH.

The first component in the composition of the present invention is a hydrophobically modified, pH responsive acrylic polymeric thickener. Examples of suitable acrylic polymeric thickeners include, but are not limited to those comprised of, based upon the total weight of the thickener,:

a) from about greater than 0 percent to less than about 100 percent of an ester of acrylic acid; an ester of methacrylic acid; an ester of itaconic acid; an ester of acrylic acid copolymerized with an alkylated or alkoxylated fatty alcohol having a straight chain alkyl group containing from about 2 to about 40, preferably from about 8 to about 35 carbon atoms, and more preferably from about 12 to about 30 carbon atoms, and a degree of ethoxylation of from about 2 to about 250 moles, preferably from about 10 to about 150 moles and more preferably from about 10 to about 50 moles; an ester of methacrylic acid copolymerized with the above-described alkoxylated fatty alcohol; an ester of itaconic acid copolymerized with the above-described alkoxylated fatty alcohol; and mixtures and copolymers thereof; and b) from about greater than 0 percent to less than about 100 percent of a monomer of acrylic acid, itaconic acid, methacrylic acid, or mixtures thereof.

Preferred acrylic polymeric thickeners include:

(1) copolymers comprised of: (a) an ester of a methacrylic acid or itaconic acid copolymerized with Steareth-20, Cetheth 20, or Steareth 20; and (b) one or more monomers of acrylic acid, methacrylic acid, itaconic acid, or mixtures thereof;

(2) copolymers comprised of (a) an alkyl acrylate having from about 10 to about 30 carbon atoms; and (b) one or more monomers of acrylic acid, methacrylic acid, itaconic acid, or mixtures thereof; and (3) copolymers comprised of mixtures of (1) and (2), wherein the copolymer of (2) is further crosslinked with an allyl ether of a polyhydroxy compound such as pentaerythritol, sucrose, or mixtures thereof.

An example of a preferred acrylic polymeric thickener is the acrylates/steareth-20 methacrylate copolymer, which is commercially available through International Specialty Products ("ISP") under the tradename, "ACULYN 22." Another example of a preferred acrylic polymeric thickener is the acrylates/ceteth-20 itaconate copolymer, which is commercially available from National Starch and Chemical Company under the tradename, "STRUCTURE 3000/3001." Yet another example of a preferred acrylic polymeric thickener is the acrylates/steareth-20 itaconate copolymer, which is commercially available from National Starch and Chemical Company under the tradename, "STRUCTURE 2000/2001." A further example of a preferred acrylic polymeric thickener is the acrylates/alkyl C10–30 acrylate copolymer, which is commercially available from B.F. Goodrich Company under the tradenames, "PEMULEN" and "CARBOPOL."

Other suitable acrylic polymeric thickeners include those set forth in U.S. Pat. No. 4,552,685, which is incorporated by reference herein. Examples of such suitable polymeric thickeners include those surfactant ester copolymers of (a) an alpha-beta ethylenically unsaturated carboxylic acid; (b) a nonionic surfactant ester of an alpha, beta ethylenically unsaturated carboxylic acid; and (c) a polymeric chain extender of an alpha, beta ethylenically unsaturated monomer copolymerizable with the unsaturated carboxylic acid and unsaturated surfactant ester. Preferably such thickeners include, based upon the total weight of the monomer thickener, from about 15 percent to about 60 percent of monomer (a), from about 1 percent to about 30 percent of monomer (b), and from about 15 percent to about 80 percent of monomer (c). to about 30 percent of monomer (b), and from about 15 percent to about 80 percent of monomer (c).

Examples of suitable alpha-beta ethylenically unsaturated carboxylic acids include those of the formula I.:

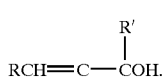

I

Wherein

R is —H, —COOX, or —CH$_3$;

R' is —H, an alkyl group having from about 2 to about 50 carbon atoms, preferably from about 6 to about 24 carbon atoms or —CH$_2$COOX; and X is —H or an alkyl group having from about 2 to about 50 carbon atoms, preferably from about 6 to about 24 carbon atoms.

Examples of suitable unsaturated surfactant esters include those of the formula II.:

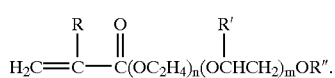

II

Wherein:

R is H or CH$_3$;

R" is an alkyl group or alkylphenyl group having from about 2 to about 50 carbon atoms, preferably from about 6 to about 24 carbon atoms.

Each R' individually is —H, —CH$_3$, or —C$_2$H$_5$;

n is an integer from about 0 to about 100;

m is an integer from about 0 to about 100; and the sum of m+n is at least 1.

Examples of suitable polymeric extender monomers include those having the formula III.:

CH$_2$=CYZ  III.

wherein:

Y is —H, —CH$_3$, or a halogen;

Z is —COOR, C$_6$H$_4$R', —Cl; —Br; —CN; or —CH=CH$_2$.

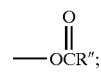

R is an alkyl group or hydroxyalkyl group having from about 2 to about 50 carbon atoms, preferably from about 6 to about 24 carbon atoms;

R' is —H, an alkyl group having from about 2 to about 50 carbon atoms, preferably from about 6 to about 24 carbon atoms; and R" is an alkyl group having from about 2 to about 50 carbon atoms, preferably from about 6 to about 24 carbon atoms.

The composition of the present invention contains, based upon the total weight of the composition, from about 0.01 percent to about 5.0 percent, preferably from about 0.1 percent to about 3.0 percent and more preferably from about 0.3 percent to about 1.0 percent of the hydrophobically modified acrylic copolymer thickener.

For purposes of minimizing irritation to the skin and/or ocular structures and tissues, the hydrophobically modified acrylic copolymer is preferably no greater than, based upon the total weight of the composition, about 1.2 percent, preferably not greater than 0.6 percent and more preferably not greater than 0.3 percent.

The second component in the composition of the present invention is a polyol alkoxy ester thickener. Examples of suitable polyol alkoxy ester thickeners include:

a) a polyethylene glycol monoesters of an alkyl acid, wherein the alkyl acid has from about 10 carbon atoms to about 24 carbon atoms, preferably from about 14 carbon atoms to about 24 carbon atoms, and more preferably from about 18 carbon atoms to about 24 carbon atoms and having an average of about 32 to about 250 moles of ethylene oxide;

b) a polyethylene glycol ether of a monoester of methyl glucose and the above-described alkyl acid having an average of between about 75 and 150 moles of ethylene oxide;

c) a polyethylene glycol ether of a diester of methyl glucose and the above-described alkyl acid having an average of between about 75 and 150 moles of ethylene oxide;

d) a polyethylene glycol ether of a triester of methyl glucose and the above-described alkyl acid having an average of between about 75 and 150 moles of ethylene oxide;

e) a polyethylene glycol ether of a quatester of methyl glucose and the above-described alkyl acid having an average of between about 75 and 150 moles of ethylene oxide; or f) mixtures thereof.

Preferred polyol alkyoxy esters include polyethylene glycol diesters of stearic acid with an average of 150 moles of ethylene oxide, which is commercially available from Stepan Company under the tradename, "KESSCO 6000"; a polyethylene glycol ether of the diester of methyl glucose and oleic acid with an average of 120 moles of ethylene oxide, which is commercially available from Amerchol Corporation under the tradename, "KESSCO 6000;" and mixtures thereof.

The polyol alkoxy ester polymeric thickener is present in the composition of the present invention at a level from, based upon the total weight of the composition, of from about 1.0 percent to about 20 percent, preferably from about 1.0 percent to about 10 percent, and more preferably from about 1.0 percent to about 5 percent.

In a preferred embodiment, the weight ratio of the hydrophobically modified acrylic copolymer thickener: polyol alkoxy ester thickener is, on an active basis, from about 3:1 to about 1:350, preferably from about 1:1 to about 1:100, and more preferably from about 1:1 to about 1:10.

The third component of the present invention is one or more surfactants comprised of an anionic surfactant, a nonionic surfactant, an amphoteric surfactant, a betaine surfactant or mixtures thereof. Examples of suitable surfactant cleansers and cleansing systems are disclosed in U.S. Pat. No. 4,443,362, which is incorporated by reference in its entirety herein. Preferably, the amount of surfactants on an active basis is, based upon the total weight of the composition, from about 2.5 percent to about 50 percent, preferably from about 5 percent to about 40 percent, and more preferably from about 8 percent to about 25 percent.

Examples of suitable classes of anionic surfactants include the alkyl sulfates, alkyl ether sulfates, sulfosuccinates, isethionates, acyl amides, alkyl ether carboxylates and alkyl phosphates, which can be employed in the present invention, on an active basis, at a level of, based upon the total weight of the composition, from about 0.1 percent to about 20 percent, preferably from about 0.5 percent to about 10 percent, and more preferably from about 0.75 percent to about 5 percent. Preferred anionic surfactants include sodium laureth sulfate, sodium trideceth sulfate, sodium laureth-13 carboxylate, disodium laureth sulfosuccinate, and mixtures thereof.

Examples of suitable nonionic surfactants include the fatty alcohol acid or amide ethoxylates, monoglyceride ethoxylates, sorbitan ester ethoxylates and alkyl polyglycosides, which can be employed in the present invention, on an active basis, at a level of, based upon the total weight of the composition, from about 0.1 percent to about 30 percent, preferably from about 0.1 percent to about 20 percent, and more preferably from about 0.1 percent to about 15 percent. Preferred nonionic surfactants include polysorbate 20, PEG-80 sorbitan laurate, decyl polyglucose, sorbitan laurate, and mixtures thereof.

Examples of suitable amphoteric surfactants include alkylimino-diprorionates, alkylamphoglycinates (mono or di), alkylamphoprorionates (mono or di), alkylamphoacetates (mono or di)N-alkyl β-aminoproprionic acids, alkylpolyamino carboxylates and phosphorylated imidazolines, which can be employed in the present invention, on an active basis, at a level of from, based upon the total weight of the composition, from about 0.1 percent to about 20 percent, preferably from about 0.1 percent to about 15 percent, and more preferably from about 0.1 percent to about 10 percent. Preferred amphoteric surfactants include sodium lauroampho pg-acetate phosphate, disodium lauroamphodiacetate, sodium carboxymethyl cocopolypropylamine and mixtures thereof.

Examples of suitable betaine surfactants include alkyl betaines, alkylamido betaines, alkyl sultaines and alkylamido sultaines, which can be employed in the present invention, on an active basis, at a level of from, based upon the total weight of the composition, from about 0.1 percent to about 15 percent, preferably from about 0.1 percent to about 10 percent, and more preferably from about 0.1 percent to about 8 percent. Preferred betaine surfactants include lauryl betaine, cocamidopropyl hydroxysultaine, cocamidopropyl betaine, and mixtures thereof.

In one preferred embodiment, the combination of surfactants includes disodium lauroamphodiacetate, sodium laureth sulfate, POE 80 sorbitan monolaurate and cocamidopropyl betaine.

The composition of the present invention may be combined with art known body or hair cleansing product ingredients to form various body and hair cleansing products such as soaps, shampoos, gels, baths, washes, creams, mousses, and the like.

When either a hydrophobically modified acrylic thickener or a polyol alkoxy ester thickener was included in the detergent composition as the sole thickener, the viscosity of the resulting detergent composition increased, but its clarity was substantially reduced relative to that of the surfactant composition devoid of any thickeners. However, a highly viscous detergent composition could not be obtained by using only a hydrophobically modified acrylic thickener as the sole thickener. With respect to clarity, the resulting clarity of a detergent composition containing only a polyol alkoxy ester as the sole thickener was relatively more hazy than that of compositions containing only a hydrophobically modified acrylic thickener as the sole thickener. It has been unexpectedly found that when a polyol alkoxy ester thickener and a hydrophobically modified acrylic thickener are combined in the detergent composition of the present invention, both the clarity and the viscosity of the resulting detergent composition are substantially improved. Since the amount of modified acrylic thickener used in the composition of the present invention is relatively low, we believe that the resulting detergent composition will also have a relatively low irritation level to the eyes and skin. Moreover, the detergent composition containing both a polyol alkoxy ester thickener and a hydrophobically modified acrylic thickener possessed a clarity that was synergistically greater than that for the same detergent composition containing only a hydrophobically modified acrylic thickener.

By "substantially improved clarity," it is meant that the light transmittance through the resulting detergent composition is increased by at least 5% relative to the transmittance through a similar composition containing only a polyol alkoxy ester thickener as measured by a UV spectrophotometer, such as a Model DU Beckman UV spectrophotometer, at a wavelength of 800 nm and utilizing a 1 cm cell. By a "solution possessing clarity", it is meant that the solution exhibits a light transmittance of at least about 50%, preferably at least about 80% and more preferably at least about 95%.

The viscosity of the resulting detergent composition of the present invention may range from about 3000 centipoise to about 50,000 centipoise, preferably from about 5000 centipoise to about 20,000 centipoise as determined using a Brookfield DV–I+Viscometer using a #4 spindle at an appropriate rotational speed (between 12 to 30 RPM). It was unexpectedly found that the detergent composition of the present invention, which contained both a polyol alkoxy ester thickener and a hydrophobically modified acrylic thickener, not only possessed a viscosity greater than that of a similar detergent composition containing either individual thickener as the sole thickening agent, but also possessed improved spreadability over a similar detergent composition thickened only with polyol alkoxy ester thickeners exclusively.

Pseudoplastic fluids, which are solutions that demonstrate decreased viscosity with increased shear rate, are typically characterized physically by their ability to spread. For example, solutions possessing a high degree of pseudoplasticity exhibit better spreadability than solutions having a lower degree of pseudoplasticity. The degree of pseudoplasticity can be determined by calculating the Index of Pseudoplasticity, which is the ratio of the viscosity of a material at a low shear rate divided by the viscosity at a high shear rate. Thus, a solution that exhibits a higher pseudoplasticty index indicates a greater degree of pseudoplasticity (shear thinning) and therefore also possesses better spreadability. We have found that the composition of the present invention unexpectedly possessed a superior Index of Pseudoplasticity, and thus superior spreadability, which is a highly favorable property of shampoos and other detergent systems, relative to similar compositions containing either a polyol alkoxy ester thickener or a hydrophobically modified acrylic copolymer thickener.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Example 1

Preparation of Detergent Composition Containing Acrylic Copolymer and PEG-150 Distearate Copolymer Preparation of Main Mixture:

After heating 40.0 parts of water in another Pyrex glass beaker to about 70 to 75° C. with agitation, 1.0 part of the acrylic copolymeric thickener was added thereto with agitation at constant temperature until the resulting solution was homogenous. 1.2 parts of PEG 6000 distearate were then added with agitation thereto at constant temperature until all of the PEG 6000 distearate was dissolved therein. While the resulting mixture was cooled to about 25° C., the following ingredients were added sequentially thereto with agitation: 10.0 parts Sodium Laureth (2) Sulfate, 4.0 parts POE 80 Sorbitan Monolaurate, 3.0 parts Disodium Lauroamphodiacetate, and 15.0 parts Cocamidopropyl Betaine. This resulting mixture was agitated until a homogeneous solution was formed. 10 parts of the pre-mixture were then added thereto with agitation at a temperature of 25° C.

After the resulting mixture was cooled to about 40° C. or less, the following components were added sequentially thereto with agitation: 0.20 parts Tetrasodium EDTA and 0.10 parts quaternium 15. The resulting mixture was cooled to approximately 25° C., then the pH of the cooled mixture was adjusted with a 20% citric acid solution until a final pH of 6.0 to 6.6 was obtained. The batch weight was then adjusted with water to achieve a total formulation of 100 parts.

The final formulation possessed a viscosity of 5 approximately 34,500 cps as measured by a Brookfield DV-I+ Viscometer using a #4 spindle at 12 RPM. The clarity was determined to be 84.3%, expressed as percent light transmittance, and was measured using a Model DU Beckman UV spectrophotometer with a 1 cm cell at a wavelength of 800 nm.

| Tradename | INCI Name | % Active | % (wt/wt) | % Active (wt/wt) |
|---|---|---|---|---|
| Monateric-949J available from Mona Industries, Inc. | Disodium Lauroamphodiacetate | 30 | 3.0 | 0.900 |
| Cedepal SN 303 available from Stepan Company | Sodium Laureth (2) Sulfate | 30 | 10.0 | 3.000 |
| Aculyn 22 available from IS | Acrylates/Steareth-20 Methacrylate Copolymer | 30 | 1.0 | 0.300 |
| KESSCO PEG 6000 DS available from Stepan Company | PEG-150 Distearate | 100 | 1.2 | 1.200 |
| Atlas G-4280 available from ICI Americas Incorporated | POE 80 Sorbitan Monolaurate | 72 | 4.0 | 2.880 |
| Ucare Polymer JR 400 available from Amerchol Corporation | Polyquaternium 10 | 100 | 0.2 | 0.200 |
| Tegobetaine L-7 available from Goldschmidt Chemical Corporation | Cocamidopropyl Betaine | 30 | 15.0 | 4.500 |
| Versene 100XL available from Dow Chemical Company | Tetrasodium EDTA | 38 | 0.20 | 0.076 |
| Dowicil 200 available from Dow Chemical Company | Quaternium 15 | 100 | 0.10 | 0.100 |
| Citric Acid, USP | Citric Acid, USP | 100 | 0.21 | 0.21 |
| Water | Water | 0 | 65.09 | 0 |

Preparation of Pre-Mix:

Component amounts in this procedure were given in terms of parts by weight to prepare 100 parts of the pre-mix. 2 parts of polyquaternium 10 were added to 98 parts of water in a Pyrex glass beaker with mixing at room temperature until the resulting pre-mixture was substantially clear and free of particulate.

Example 2

Preparation of Acrylate Copolymer-Free Detergent Composition Containing PEG-150 Distearate The solution of Example 2 was prepared in accordance with the procedure set forth in Example 1 using the components set forth below:

| Tradename | INCI Name | % Active | % (wt/wt) | % Active (wt/wt) |
|---|---|---|---|---|
| Monateric-949J available from Mona Induatries, Inc. | Disodium Lauroamphodiacetate | 30 | 3.0 | 0.900 |
| Cedepal SN 303 available from Stepan Company | Sodium Laureth (2) Sulfate | 30 | 10.0 | 3.000 |
| KESSCO PEG 6000 DS available from Stepan Company | PEG-150 Distearate | 100 | 1.2 | 1.200 |
| Atlas G-4280 available from ICI | POE 80 Sorbitan Monolaurate | 72 | 4.0 | 2.880 |
| Ucare Polymer JR 400 available from Amerchol Corporation | Polyquaternium 10 | 100 | 0.2 | 0.200 |
| Tegobetaine L-7 available from Goldschmidt Chemical Corporation | Cocamidopropyl Betaine | 30 | 15.0 | 4.500 |
| Versene 100XL available from Dow Chemical Company | Tetrasodium EDTA | 38 | 0.20 | 0.076 |
| Dowicil 200 available from Dow Chemical Company | Quaternium 15 | 100 | 0.10 | 0.100 |
| Citric Acid, USP | Citric Acid, USP | 100 | 0.38 | 0.38 |
| Water | Water | 0 | 65.92 | 0 |

The resulting solution possessed a viscosity of approximately 18,900 cps as measured by a Brookfield DV-I+ Viscometer using a #4 spindle at 12 RPM. The clarity of the solution was determined to have a 71.6% light transmittance as measured using an Model DU Beckman UV spectrophotometer with a 1 cm cell at a wavelength of 800 nm. Comparative results for Examples #1 and #2 are summarized in Table I below:

TABLE I

Viscosity and Clarity Comparison

| Example # | Acrylic Copolymeric Thickener (w/w % active) | Polyol Alkoxy Ester Thickener (w/w % active) | Viscosity (cps)* | Clarity (% transmittance)** |
|---|---|---|---|---|
| Example #1 | Aculyn 22 (0.6) | PEG 6000 Distearate (1.2) | 34,500[1] | 84.3 |
| Example #2 | — | PEG 6000 Distearate (1.2) | 18,900[1] | 71.6 |

*Measured using a Brookfield DV-I+ Viscometer using a #4 spindle at 12 RPM.
**Measured using an UV spectrophotometer with a 1 cm cell at 800 nm wavelength.

This Example shows that the detergent composition containing both a polyol alkoxy ester and an acrylic copolymer was significantly clearer relative to similar compositions devoid of the acrylic copolymer thickener.

Example 3

Preparation of Detergent Compositions, With and Without Polyol Alkoxy Ester Thickeners and/or Acrylate Copolymer Thickeners Separate portions of a commercially available baby shampoo sold by Johnson & Johnson Consumer Companies, Inc. under the tradename "No More Tears"® Baby Shampoo, which contained water, PEG-80 Laurate, Cocamidopropyl Betaine, Sodium Trideceth Sulfate, Glycerin, Disodium Lauroamphodiacetate, PEG-150 Distearate, Sodium Laureth-13 Carboxylate, Fragrance, Polyquaternium-10, Tetrasodium EDTA, Quaternium-15, Citric Acid, D&C Yellow #10 and D&C Orange #4, were added to various thickener combinations as described in Table II in order to form several thickened surfactant cleansing compositions. The thickened cleansing compositions were tested for clarity and viscosity and results summarized in Table II.

TABLE II

Viscosity and Clarity Comparison for Compositions Containing Various Thickeners*

| Sample # | Total Concentration of Acrylic Copolymeric Thickener (% w/w active) | Total Concentration of First Polyol Alkoxy Ester Thickener (% w/w active) | Total Concentration of Second Polyol Alkoxy Ester Thickener (% w/w active) | Viscosity (cps) | Clarity[4] (% transmittance) |
|---|---|---|---|---|---|
| 3-1[8] | Acrylate/steareth 20 methacrylate copolymer[5] (0.6) | PEG-120 methylglucose dioleate[6] (2.0) | — | 10,700[2] | 97.8% |
| 3-2[8] | — | PEG-120 methylglucose dioleate[6] (2.0) | — | 5780[2] | 71.4% |

TABLE II-continued

Viscosity and Clarity Comparison for
Compositions Containing Various Thickeners*

| Sample # | Total Concentration of Acrylic Copolymeric Thickener (% w/w active) | Total Concentration of First Polyol Alkoxy Ester Thickener (% w/w active) | Total Concentration of Second Polyol Alkoxy Ester Thickener (% w/w active) | Viscosity (cps) | Clarity[4] (% transmittance) |
|---|---|---|---|---|---|
| 3-3 | Acrylate/steareth 20 methacrylate copolymer[5] (0.6) | PEG-120 methylglucose dioleate[6] (2.0) | PEG 6000 Distearate[7] (2.0) | 40,450[1] | 100% |
| 3-4 | — | PEG-120 methylglucose dioleate[6] (2.0)) | PEG 6000 Distearate[7] (2.0) | 28,350[1] | 71.4% |
| 3-5[8] | Acrylate/steareth 20 methacrylate copolymer[5] (0.6) | — | — | 1120[3] | 98.9% |
| 3-6 | Acrylate/steareth 20 methacrylate copolymer[5] (1.2) | — | — | 4500[2] | 97.4% |

[1]Measured using a Brookfield DV-I+ Viscometer using a #4 spindle at 12 RPM.
[2]Measured using a Brookfield DV-I+ Viscometer using a #4 spindle at 30 RPM.
[3]Measured using a Brookfield DV-I+ Viscometer using a #2 spindle at 12 PRM.
[4]Measured using an UV spectrophotometer with a 1 cm cell at 800 nm wavelength.
[5]Available from ISP under the tradename, "Aculyn 22."
[6]Available from Amerchol Corporation under the tradename, "Glucamate DOE 120 ."
[7]Available from Stepan Company under the tradename, "KESSCO 6000."
[8]PEG-150 Distearate was removed from the Johnson's Baby Shampoo
*Remainder of composition comprised of the identified shampoo.

This Example shows that the detergent compositions, which were thickened with only one or more polyol alkoxy ester thickeners, were relatively hazy. However, upon the addition of an acrylate copolymeric thickener thereto, the resulting polyol alkoxy ester-containing compositions became relatively more clear and viscous. Moreover, as shown in Examples 3-4 and 3-5 relative to Example 3-3, the detergent compositions containing both thickeners (Example 3-3) unexpectedly possessed a clarity that is superior to that of the composition containing only acrylate copolymer thickener (Example 3-5).

This Example further shows that the detergent compositions containing only the acrylate/steareth 20 methacrylate thickener at relatively low levels were clear; however, the viscosity of the resulting composition was below the acceptable range for a gel. Yet, as the amount of the acrylate/steareth 20 methacrylate thickener was increased as shown in Example 3-6, the clarity of the resulting detergent composition not only was reduced, but the resulting composition also failed to possess the requisite viscosity desired in a gel.

This Example further shows that in composition containing the acrylic copolymer thickener as the sole thickener, the clarity of the resulting composition was decreased as the amount of acrylic copolymer was increased (Examples 3-5 and 3-6).

Example 4

Comparative Psuedoplasticity Tests

About 1 ml of each respective solution of Example 3 were placed on the lower plate of a Haake Model PK 100 viscometer with cone (PK I, 1°) and plate geometry at a temperature of 25° C. Over a two minute period, the shear rate of the cone was varied from 0 to $1500^{-1}$ seconds, in a linear fashion, and the viscosity of the solution measured at $100^{-1}$ seconds and $1000^{-1}$ seconds. The Index of Pseudoplasticity, which is the ratio of the viscosity of a material at a low shear rate divided by the viscosity at a high shear rate, was then calculated as the viscosity at $100^{-1}$ seconds divided by the viscosity at $1000^{-1}$ seconds, and the results are set forth below in Table III:

TABLE III

Viscosity and Index of Pseudoplasticity

| Sample No. | Acrylic Copolymeric Thickener* (% w/w active) | 1st Polyol Alkoxy Ester Thickener* (% w/w active) | 2nd Polyol Alkoxy Ester Thickener* (% w/w active) | Viscosity @ $100^{-1}$ Seconds (cps)[1] | Viscosity @ $1000^{-1}$ Seconds (cps)[1] | Index of Pseudo-Plasticity[1] |
|---|---|---|---|---|---|---|
| 3-1 | Acrylate/steareth 20 | PEG-120 methylglucose | — | 6752 | 436.0 | 15.5 |

TABLE III-continued

Viscosity and Index of Pseudoplasticity

| Sample No. | Acrylic Copolymeric Thickener* (% w/w active) | 1st Polyol Alkoxy Ester Thickener* (% w/w active) | 2nd Polyol Alkoxy Thickener* (% w/w active) | Viscosity @ $100^{-1}$ Seconds (cps)[1] | Viscosity @ $1000^{-1}$ Seconds (cps)[1] | Index of Pseudo-Plasticity[1] |
|---|---|---|---|---|---|---|
| | methacrylate copolymer (0.6) | dioleate (2.0) | | | | |
| 3-2 | — | PEG-120 methylglucose dioleate (2.0) | — | 3273 | 841.9 | 3.9 |
| 3-3 | Acrylate/steareth 20 methacrylate copolymer (0.6) | PEG-120 methylglucose dioleate (2.0) | PEG 6000 Distearate (2.0) | 18,660 | 156.0 | 119.6 |
| 3-4 | — | PEG-120 methylglucose dioleate (2.0)) | PEG 6000 Distearate (2.0) | 14,050 | 405.6 | 34.6 |
| 3-5 | Acrylate/steareth 20 methacrylate copolymer (0.6) | — | — | 969.9 | 455.1 | 2.1 |
| 3-6 | Acrylate/steareth 20 methacrylate copolymer (1.2) | — | — | 3170 | 1107 | 2.9 |

[1]Calculated as viscosity at 100 seconds divided by the viscosity at $1000^{-1}$ seconds.
*Expressed in terms of total weight concentration This Example shows that formulations containing both the acrylic copolymer thickener and the polyol alkoxy ester (Sample # 3-1) possessed a higher index of pseudoplasticity and thus superior spreadability, relative to either a similar formulation containing a polyol alkoxy ester as the sole thickener (Sample #3-2) or a formulation containing an acrylic copolymer as the sole thickener (Sample #3-5). Therefore, it is clearly apparent that cleansing systems that contain a hydrophobically modified acrylic thickener with a polyol alkoxy ester thickener possessed surprisingly superior spreadability, as determined by the Index of Pseudoplasticity, than a similar cleansing system possessing either thickener as the sole thickening agent.

Similarly, this Example further shows that the formulation containing a hydrophobically modified acrylic thickener along with two polyol alkoxy ester thickeners (Sample #3-3) possessed a relatively higher Index of Pseudoplasticity, and thus superior spreadability, than that for a similar formulation containing either the same two polyol alkoxy ester thickeners but no acrylic copolymer thickener (Sample # 3-4) or only the acrylic copolymer thickener (Sample #3-5). Therefore, it is further apparent that cleansing systems that contain the both a hydrophobically modified acrylic thickener with two polyol alkoxy ester thickeners possess surprisingly better spreadability than a similar cleansing system possessing either the hydrophobically modified acrylic thickener or both of the two polyol alkoxy ester thickeners as the sole thickening agent(s).

In sum, this Example shows that the formulations that contain both a polyol alkoxy ester thickener with a hydrophobically modified acrylic thickener have improved shear thinning or spreadability, and thus affect an improvement on the overall rheology of the cleansing system.

We claim:
1. A detergent composition comprising:
   a) a hydrophobically modified acrylic copolymer thickener;
   b) a polyol alkoxy ester thickener; and
   c) at least one surfactant selected from the group consisting of an anionic surfactant, a non-ionic surfactant, an amphoteric surfactant, a betaine surfactant, and mixtures thereof, wherein the composition contains greater than about 1%, based upon the total weight of the composition, of the polyol alkoxy ester thickener and
wherein the polyol alkoxy ester is selected from:
   a) a polyethylene glycol ether of a monoester of methyl glucose and an alkyl acid having from about 10 carbon atoms to about 24 carbon atoms and having an average of between about 75 and 150 moles of ethylene oxide;
   b) a polyethylene glycol ether of a diester of methyl glucose and an alkyl acid having from about 10 carbon atoms to about 24 carbon atoms and having an average of between about 75 and 150 moles of ethylene oxide;
   c) a polyethylene glycol ether of a triester of methyl glucose and an alkyl acid having from about 10 carbon atoms to about 24 carbon atoms and having an average of between about 75 and 150 moles of ethylene oxide; and
   d) mixtures thereof.

2. The composition of claim 1 wherein the acrylic copolymer thickener is comprised of:
   a) a first monomer selected from: an ester of acrylic acid; an ester of methacrylic acid; an ester of itaconic acid; an ester of acrylic acid copolymerized with an alkylated or alkoxylated fatty alcohol having a straight chain alkyl group containing from about 2 carbon atoms to about 40 carbon atoms and a degree of ethoxylation of from about 2 to about 250 moles; an ester of methacrylic acid copolymerized with an alkylated or alkoxylated fatty alcohol having a straight chain alkyl group containing from about 2 carbon atoms to about 40 carbon atoms and a degree of ethoxylation of from about 2 to about 250 moles; an ester of itaconic acid copolymerized with an alkylated or alkoxylated fatty alcohol having a straight chain alkyl group containing from about 2 carbon atoms to about 40 carbon atoms and a degree of ethoxylation of from about 2 to about 250 moles; and mixtures and copolymers thereof; and b) acrylic acid, methacrylic acid, itaconic acid, and mixtures thereof.

3. The composition of claim 1 wherein the acrylic copolymer thickener is comprised of:

A) a copolymer comprised of:
1) an ester of a methacrylic acid or itaconic acid copolymerized with Ceteth 20 or Steareth 20; and
2) one or more monomers of acrylic acid, methacrylic acid, itaconic acid, or mixtures thereof;

B) a copolymer of
1) an alkyl acrylate having from about 10 to about 30 carbon atoms; and 2) one or more monomers of acrylic acid, methacrylic acid, itaconic acid, or mixtures thereof, wherein the copolymer of (B) is further crosslinked with an allyl ether of a polyhydroxy compound; and C) mixtures and copolymers thereof.

4. The composition of claim 1 wherein the acrylic copolymer thickener is selected from A.) acrylates/steareth-20 methacrylate copolymer;

B.) acrylates/ceteth-20 itaconate copolymer;

C.) acrylates/steareth-20 itaconate copolymer;

D.) acrylates/alkyl C10-30 acrylate copolymer; and

E.) mixtures and copolymers thereof.

5. The composition of claim 1 wherein the acrylic copolymer thickener is comprised of A) an alpha-beta ethylenically unsaturated carboxylic acid monomer;

B) a nonionic surfactant ester of an alpha, beta ethylenically unsaturated carboxylic acid monomer; and C) a polymeric chain extender of an alpha, beta ethylenically unsaturated monomer copolymerizable with the unsaturated carboxylic acid and unsaturated surfactant ester.

6. The composition of claim 5 wherein the acrylic copolymer thickener is comprised of, based upon the total weight of acrylic copolymer thickener:

A.) from about 15 percent to about 60 percent of monomer (A);

B.) from about 1 percent to about 30 percent of monomer (B); and

C.) from about 15 percent to about 80 percent of monomer (C).

7. The composition of claim 5, wherein the alpha-beta ethylenically unsaturated carboxylic acids include those of the formula I.:

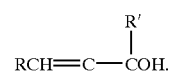

wherein
R is —H, —COOX, or —CH$_3$;
R' is —H, an alkyl group having from about 2 to about 50 carbon atoms or —CH$_2$COOX;
X is —H or an alkyl group having from about 2 to about 50 carbon atoms.

8. The composition of claim 5, wherein the unsaturated surfactant esters include those of the formula II.:

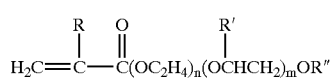

wherein:
R is H or CH$_3$;
R" is an alkyl group or alkylphenyl group having from about 2 to about 50 carbon atoms;
Each R' individually is —H, —CH$_3$, or —C$_2$H$_5$;
n is an integer from 0 to about 100;
m is an integer from 0 to about 100; and
the sum of m+n is at least 1.

9. The composition of claim 5, wherein the polymeric extender monomers include those having the formula III.:

wherein:
Y is —H, —CH$_3$, or a halogen;
Z is —COOR, C$_6$H$_4$R', —Cl; —Br; —CN; O or —CH=CH$_2$;

R is an alkyl group or hydroxyalkyl group having from about 2 to about 50 carbon atoms;
R' is —H, an alkyl group having from about 2 to about 50 carbon; and
R" is an alkyl group having from about 2 to about 50 carbon atoms.

10. The composition of claim 1, wherein the acrylic copolymer thickener is present in an amount, based upon the total weight of the composition, from about 0.01 percent to about 5.0 percent.

11. The composition of claim 1, wherein the acrylic copolymer thickener is present in an amount, based upon the total weight of the composition, from about 0.1 percent to about 3.0 percent.

12. The composition of claim 1, wherein the acrylic copolymer thickener is present in an amount, based upon the total weight of the composition, not to exceed 1.2 percent.

13. The composition of claim 1, wherein the acrylic copolymer thickener is present in an amount, based upon the total weight of the composition, not to exceed 0.3 percent.

14. The composition of claim 1, wherein the polyol alkoxy ester is
a polyethylene glycol ether of the diester of methyl glucose and oleic acid with an average of 120 moles of ethylene.

15. The composition of claim 1 wherein the polyol alkoxy ester thickener is present in the composition at a level, based upon the total weight of the composition, of from about 1.0 percent to about 20 percent.

16. The composition of claim 15 wherein the polyol alkoxy ester thickener is present in the composition at a level, based upon the total weight of the composition, of from about 1.0 percent to about 5 percent.

17. The composition of claim 1 wherein the weight ratio of the hydrophobically modified acrylic copolymer thickener: polyol alkoxy ester thickener is, on an active basis, from about 3:1 to about 1:350.

18. The composition of claim 17, wherein the weight ratio of the hydrophobically modified acrylic copolymer thickener: polyol alkoxy ester thickener is, on an active basis, from about 1:1 to about 1:10.

19. The composition of claim 1 wherein the composition contains the surfactant in an amount, based upon the total weight of the composition, from about 2.5 percent to about 50 percent.

20. The composition of claim 19 wherein the composition contains at least one surfactant selected from:
    a) an anionic surfactant selected from sodium laureth sulfate, sodium trideceth sulfate, sodium laureth-13 carboxylate, disodium laureth sulfosuccinate, and mixtures thereof;
    b) a nonionic surfactant selected from polysorbate 20, PEG-80 sorbitan laurate, decyl polyglucose, sorbitan laurate, and mixtures thereof;
    c) an amphoteric surfactant selected from sodium lauroampho pg-acetate phosphate, disodium lauroamphodiacetate, sodium carboxymethyl cocopolypropylamine and mixtures thereof; and
    d) a betaine surfactant selected from lauryl betaine, cocamidopropyl hydroxysultaine, cocamidopropyl betaine, and mixtures thereof.

21. The composition of claim 1 having a light transmittance of greater than 98 percent.

22. The composition of claim 1 wherein said composition is in the form of an article of manufacture.

23. The composition of claim 22, wherein said article of manufacture is in the form of a soap, shampoo, gel, bath, wash, cream, or mousse.

24. A method for improving the clarity of a polyol alkoxy ester-containing detergent composition, wherein the polyol alkoxy ester is selected from:
    a) a polyethylene glycol monoesters of an alkyl acid having from about 10 carbon atoms to about 24 carbon atoms and an average of about 32 to about 250 moles of ethylene oxide;
    b) a polyethylene glycol ether of a monoester of methyl glucose and an alkyl acid having from about 10 carbon atoms to about 24 carbon atoms and having an average of between about 75 and 150 moles of ethylene oxide;
    c) a polyethylene glycol ether of a diester of methyl glucose and an alkyl acid having from about 10 carbon atoms to about 24 carbon atoms and having an average of between about 75 and 150 moles of ethylene oxide;
    d) a polyethylene glycol ether of a triester of methyl glucose and an alkyl acid having from about 10 carbon atoms to about 24 carbon atoms and having an average of between about 75 and 150 moles of ethylene oxide; and
    e) a polyethylene glycol diester of stearic acid with an average of 150 moles of ethylene oxide; and
    f) mixtures thereof, wherein the detergent composition has a viscosity of from about 20,000 cps to about 50,000 cps comprised of:
        a) adding a sufficient amount of a hydrophobically modified acrylic thickener thereto under conditions sufficient.

25. The method of claim 24, wherein said hydrophobically modified acrylic thickener is added to a detergent composition, followed by the addition of the polyol alkoxy ester thereto.

26. A method for improving the spreadability of a detergent composition comprised of
    a) adding a sufficient amount of a hydrophabically modified acrylic thickener and a sufficient amount of a polyol alkoxy ester to the detergent composition under conditions sufficient, wherein the polyol alkoxy ester is selected from:
    a) a polyethylene glycol monoesters of an alkyl acid having from about 10 carbon atoms to about 24 carbon atoms and an average of about 32 to about 250 moles of ethylene oxide;
    b) a polyethylene glycol ether of a monoester of methyl glucose and an alkyl acid having from about 10 carbon atoms to about 24 carbon atoms and having an average of between about 75 and 150 moles of ethylene oxide;
    c) a polyethylene glycol ether of a diester of methyl glucose and en alkyl acid having from about 10 carbon stoma to about 24 carbon atoms and having an average of between about 75 and 150 moles of ethylene oxide;
    d) a polyethylene glycol ether of a triester of methyl glucose and an alkyl acid having from about 10 carbon atoms to about 24 carbon atoms and having an average of between about 75 and 150 moles of ethylene oxide;
    e) a polyethylene glycol diester of stearic acid with an average of 150 moles of ethylene oxide; and
    f) mixtures thereof, wherein the detergent composition has a viscosity of from about 20,000 cps to about 50,000 cps.

27. A method for thickening a detergent composition comprising adding a sufficient amount of a hydrophobically modified acrylic thickener and a sufficient amount of a polyol alkoxy ester to the detergent composition under conditions sufficient, wherein the polyol alkoxy ester is selected from:
    a) a polyethylene glycol monoesters of an alkyl acid having from about 10 carbon atoms to about 24 carbon atoms and an average of about 32 to about 250 moles of ethylene oxide;
    b) a polyethylene glycol ether of a monoester of methyl glucose and an alkyl acid having from about 10 carbon atoms to about 24 carbon atoms and having an average of between about 75 and 150 moles of ethylene oxide;
    c) a polyethylene glycol ether of a diester of methyl glucose and an alkyl acid having from about 10 carbon atoms to about 24 carbon atoms and having an average of between about 75 and 150 moles of ethylene oxide;
    d) a polyethylene glycol ether of a triester of methyl glucose and an alkyl acid having from about 10 carbon atoms to about 24 carbon atoms and having an average of between about 75 and 150 moles of ethylene oxide;
    e) a polyethylene glycol diester of stearic acid with an average of 150 moles of ethylene oxide; and
    f) mixtures thereof, wherein the detergent composition has a viscosity of from about 20,000 cps to about 50,000 cps.

28. A detergent composition comprising:
   a) a hydrophobically modified acrylic copolymer thickener;
   b) a polyol alkoxy ester thickener; and
   c) at least one surfactant selected from the group consisting of an anionic surfactant, a non-ionic surfactant, an amphoteric surfactant, a betaine surfactant, and mixtures thereof, wherein the composition contains greater than about 1%, based upon the total weight of the composition, of the polyol alkoxy ester thickener and wherein the polyol alkoxy ester is selected from:
   a) a polyethylene glycol monoesters of an alkyl acid having from about 10 carbon atoms to about 24 carbon atoms and an average of about 32 to about 250 moles of ethylene oxide;
   b) a polyethylene glycol ether of a monoester of methyl glucose and an alkyl acid having from about 10 carbon atoms to about 24 carbon atoms and having an average of between about 75 and 150 moles of ethylene oxide;
   c) a polyethylene glycol ether of a diester of methyl glucose and an alkyl acid having from about 10 carbon atoms to about 24 carbon atoms and having an average of between about 75 and 150 moles of ethylene oxide;
   d) a polyethylene glycol ether of a triester of methyl glucose and an alkyl acid having from about 10 carbon atoms to about 24 carbon atoms and having an average of between about 75 and 150 moles of ethylene oxide;
   e) a polyethylene glycol diester of stearic acid with an average of 150 moles of ethylene oxide; and
   f) mixtures thereof, wherein the detergent composition has a viscosity of from about 20,000 cps to about 50,000 cps.

29. The composition of claim 28, wherein the polyol alkoxy ester is selected from:
   a) polyethylene glycol diesters of stearic acid with an average of 150 moles of ethylene oxide;
   b) a polyethylene glycol ether of the diester of methyl glucose and oleic acid with an average of 120 moles of ethylene oxide; and
   c) mixtures thereof.

* * * * *